United States Patent [19]

Hiller et al.

[11] Patent Number: 5,606,169
[45] Date of Patent: Feb. 25, 1997

[54] ULTRAVIOLET LIGHT STERILIZATION RETROFIT FOR PAPERBOARD PACKAGING FILLING MACHINES

[75] Inventors: James A. Hiller, Williamsport, Pa.; Richard L. Lewis, Covington; Thomas S. Williams, III, Richmond, both of Va.

[73] Assignee: Westvaco Corporation, New York, N.Y.

[21] Appl. No.: 533,505

[22] Filed: Sep. 25, 1995

[51] Int. Cl.[6] .............................. B65B 55/08; A61L 2/10
[52] U.S. Cl. .................... 250/455.11; 250/442.1; 250/504 R; 53/425; 422/24
[58] Field of Search .................... 250/455.11, 492.1, 250/504 R; 53/425, 426; 422/24

[56] References Cited

U.S. PATENT DOCUMENTS

| | | | |
|---|---|---|---|
| 3,305,130 | 2/1967 | Meek | 221/175 |
| 3,513,627 | 5/1970 | Douchette et al. | 53/180 |
| 3,733,709 | 5/1973 | Bassemir et al. | 250/504 R |
| 3,826,014 | 7/1974 | Helding | 250/504 R |
| 3,947,249 | 3/1976 | Egger | 21/92 |
| 4,101,424 | 7/1978 | Schooley et al. | 250/504 R |
| 4,104,024 | 8/1978 | Vogele et al. | 21/58 |
| 4,171,604 | 10/1979 | Weikert | 53/426 |
| 4,175,140 | 11/1979 | Bachmann et al. | 426/399 |
| 4,375,145 | 3/1983 | Mosse et al. | 53/425 |
| 4,396,582 | 8/1983 | Kodera | 422/300 |
| 4,409,188 | 10/1983 | Silberzahn | 422/303 |
| 4,424,188 | 1/1984 | DiGeronimo | 422/20 |
| 4,786,812 | 11/1988 | Humphreys | 250/455.11 |
| 4,832,965 | 5/1989 | Helin | 426/66 |
| 4,981,649 | 1/1991 | Shibauchi et al. | 422/24 |
| 5,069,017 | 12/1991 | Fabricius | 53/426 |
| 5,122,340 | 6/1992 | Shimamura et al. | 422/28 |
| 5,129,212 | 7/1992 | Duffey et al. | 53/426 |
| 5,326,542 | 7/1994 | Sizer et al. | 422/291 |

FOREIGN PATENT DOCUMENTS

| | | |
|---|---|---|
| 1036315 | 8/1978 | Canada. |
| 1053437 | 5/1979 | Canada. |
| 61-244702 | 10/1986 | Japan. |
| 1531139 | 11/1978 | United Kingdom. |

OTHER PUBLICATIONS

UV Unit Takes the Heat Out of Sterilisation, Circle No.: Q12–160.

Romeo T. Toledo, Update on Container and Equipment Sterilization Techniques in Aseptic Packaging, *The American Institute of Chemical Engineers*, pp. 31–41.

Paul Dearborn, International Paper Company's Extended Shelf–Life Packaging, *Packaging Technology*, Mar./Apr. 1983, pp. 26–27.

Dr. L. J. Bonis and Mr. G. V. Courville, High Performance Coextrusions for the Aseptic Packaging Industry, 1983 Paper Synthetics Conference, *Tappi Proceedings*, 1983, pp. 233–243.

Keith A. Ito and K. E. Stevenson, Sterilization of Packaging Materials Using Aseptic Systems, *Food Technology*, vol. 38, No. 3, Mar. 1984, pp. 60–62.

Daniel J. Wise, Aseptic Packages, 1984 Extrusion, Coating, *Tappi Short Course Notes*, pp. 49–52.

G. Buteux, The Aseptic Filling Concept for Your Own Package, *Tappi Proceedings*, 1984 Polymers, Laminations and Coatings Conference, pp. 431–435.

Walter Schoch, Aseptic Packaging, *Tappi Journal*, vol. 67 No. 9, Sep. 1984, pp. 56–60.

(List continued on next page.)

*Primary Examiner*—Jack I. Berman
*Attorney, Agent, or Firm*—J. R. McDaniel; R. L. Schmalz

[57] ABSTRACT

This invention relates to a retrofit apparatus utilized in Ultraviolet (UV) light sterilization equipment for paperboard packaging filling machines. Such structures of this type, generally, allow conventional paperboard packaging filling machines to be economically converted to include an ultraviolet light sterilization retrofit assembly wherein microbiological spoilage of the food product contained within the paperboard packaging can be significantly reduced.

6 Claims, 3 Drawing Sheets

OTHER PUBLICATIONS

Bill Guise, Aseptic Packaging, *Converter*, Oct. 1984, pp. 6–9.

Bill Guise, Sterilised Methods Used in Packaging, Converter, Jun. 1986, pp. 15–17.

G. Cerny, Testing of Aseptic Machines for Efficiency of Sterilization of Packaging Materials by Means of Hydrogen Peroxide, *Paper Technology and Science*, vol. 5 (1992), pp. 77–81.

Extended Shelf Life Improves Market Reach, 34 *Australian Packaging*, Feb. 1993, (25 on Inform. Card).

ULTRAVIOLET LIGHT STERILIZATION RETROFIT FOR PAPERBOARD PACKAGING FILLING MACHINES

BACKGROUND OF THE INVENTION

1. Field of the Invention

This invention relates to a retrofit apparatus utilized in Ultraviolet (UV) light sterilization equipment for paperboard packaging filling machines. Such structures of this type, generally, allow conventional paperboard packaging filling machines to be economically converted to include an ultraviolet light sterilization retrofit assembly wherein microbiological spoilage of the food product contained within the paperboard packaging can be significantly reduced.

2. Description of the Related Art

It is known, in food package sterilization systems, to employ an ultraviolet (UV) sterilization means. Exemplary of such prior art sterilization systems is U.S. Pat. No. 5,326,542 ('542), to C. E. Sizer et al., entitled "Method and Apparatus for Sterilizing Cartons". While the '542 patent employs a UV lamp, the UV lamp is cooled by circulating air which has been shown to be inefficient. Due to the shear number of paperboard packages which need to be sterilized on a typical filling machine, namely, approximately 100 per minute, the air circulation does not provide adequate cooling for the UV lamp and may adversely effect the sterilizing characteristics of the UV lamp. Consequently, a more advantageous sterilization system, then, would be presented if the circulating air cooling means were replaced.

Also, it is well known to locate sterilization equipment along a food product filling line in order to sterilize the packages before the food is placed in the package. However, older filling machines, typically, do not include a UV sterilization station. Consequently, due to the physical structure of the older machines, there is very little room, if any, remaining to insert a sterilization unit. To complicate this even further, up to the present, all retrofit UV sterilization systems have been located such that they are parallel to the direction of travel of the packages to be sterilized which makes retrofitting into a confined space very difficult. Therefore, a still further advantageous sterilization system, then, would be presented if the system could easily be retrofitted into existing filling machines.

It is apparent from the above that there exists a need in the art for a sterilization system which is easily retrofitted into existing filling machines, and which at least equals the sterilizing characteristics of the known sterilization systems, but which at the same time includes adequate cooling capacity. It is the purpose of this invention to fulfill this and other needs in the art in a manner more apparent to the skilled artisan once given the following disclosure.

SUMMARY OF THE INVENTION

Generally speaking, this invention fulfills these needs by providing a retrofit assembly for ultraviolet light sterilization of paper packages, comprising an ultraviolet light means, a light retaining means operatively attached to the light means, a light covering means operatively connected to the light retaining means, and a paper package transportation means located a predetermined distance away from the light means in order that the light means can sterilize a predetermined portion of the paper package.

In certain preferred embodiments, the ultraviolet light means includes an ultraviolet lamp, lamp tube, and a lamp holder. Also, the light retaining means includes a mounting plate and a light cooling means. Finally, the light covering means includes moveable shutters.

In another further preferred embodiment, substantially all of the microorganisms present on the inner surface of the paperboard cartons are eliminated through the use of the retrofit assembly by ultraviolet light sterilization.

The preferred retrofit assembly, according to this invention, offers the following advantages: lightness in weight; ease of assembly and repair; excellent sterilization characteristics; good stability; good durability; excellent retrofit capability; excellent economy; and excellent safety characteristics. In fact, in many of the preferred embodiments, these factors of lightness in weight, sterilization, retrofit capability, and safety are optimized to an extent that is considerably higher than heretofore achieved in prior, known retrofit assemblies using ultraviolet light sterilization.

The above and other features of the present invention, which will become more apparent as the description proceeds, are best understood by considering the following detailed description in conjunction with the accompanying drawings, wherein like characters represent like parts throughout the several views and in which:

DETAILED DESCRIPTION OF THE INVENTION

Figure 1:
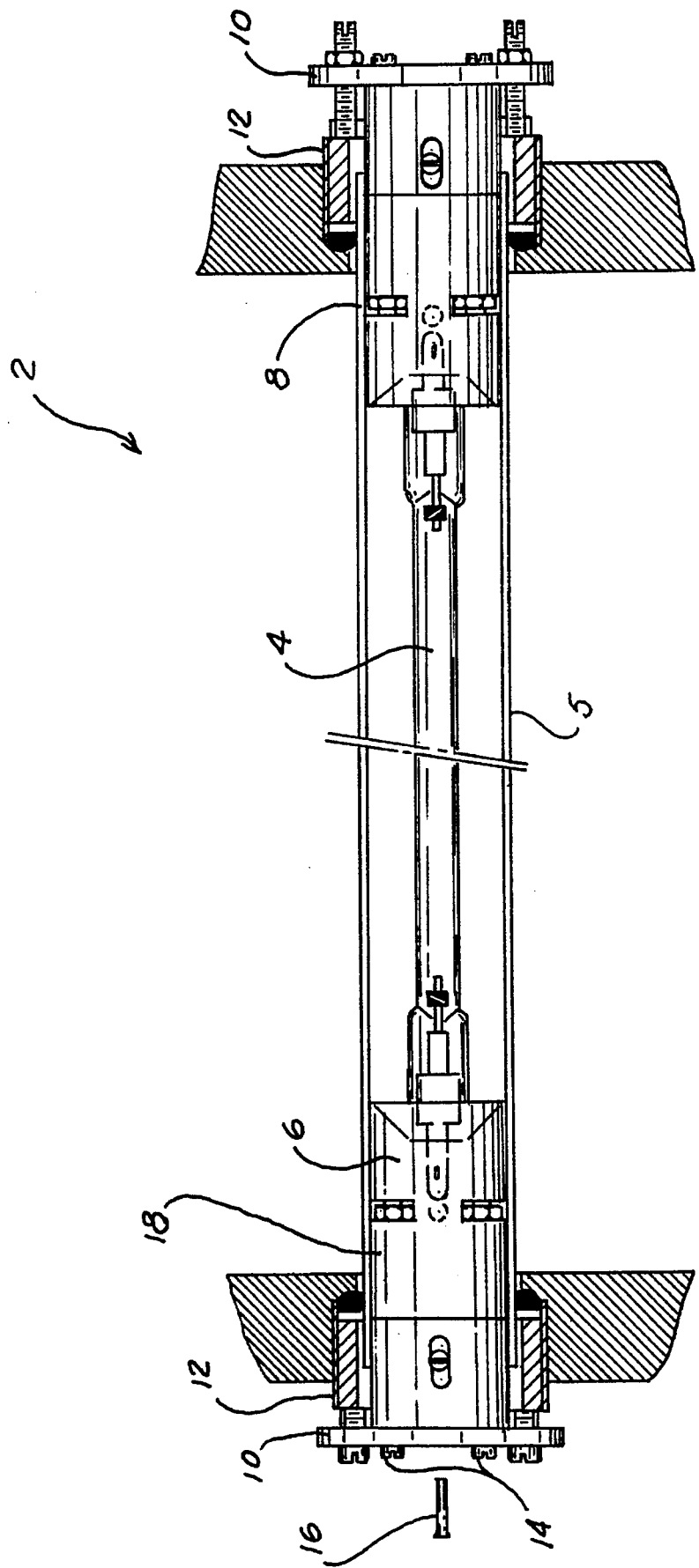
FIG. 1 is a side plan view of an ultraviolet light holder, according to the present invention.

With reference first to FIG. 1, there is illustrated ultraviolet (UV) lamp holder 2. Lamp holder 2 includes, in part, conventional UV lamp 4, lamp tube 5, lamp holder 6, conventional fasteners 8, end plates 10, conventional bushing sleeves 12, conventional fasteners 14 and 16, and conventional thermocouple 18.

During the construction of lamp holder 2, lamp 4 is retained within lamp holder 6 by fasteners 8. Lamp holder 6 is then attached to plate 10 by bushing sleeves 12 and fasteners 14 and 16. Lamp tube 5 surrounds lamp 4 and provides a conduit for the water cooling of lamp 4 which will be discussed later. Thermocouple 18 is used to regulate the temperature of lamp 4, according to conventional techniques.

Figure 2:
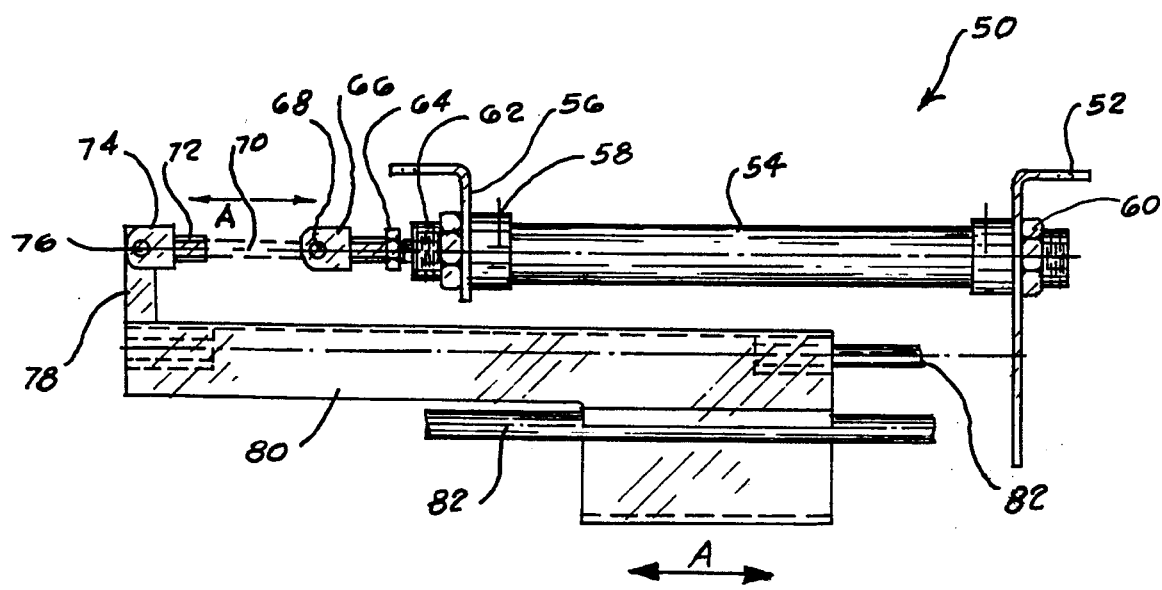
FIG. 2 is a side view of the retrofit assembly for an ultraviolet light sterilization system, according to the present invention.

FIG. 2 illustrates shutter assembly 50. Assembly 50 includes, in part, mounting bracket 52, conventional pneumatic cylinder 54, mounting bracket 56, conventional pneumatic connection 58, conventional fastener 60, conventional threader connector 62 conventional fastener 64, fork 66, slot 68, conventional rod 70, conventional sleeve 72, fork 74, slot 76 bracket 78, shutter 80, and guiding rods 82. Also the direction of travel (Arrow A) of shutter 80 is shown.

Figure 3:
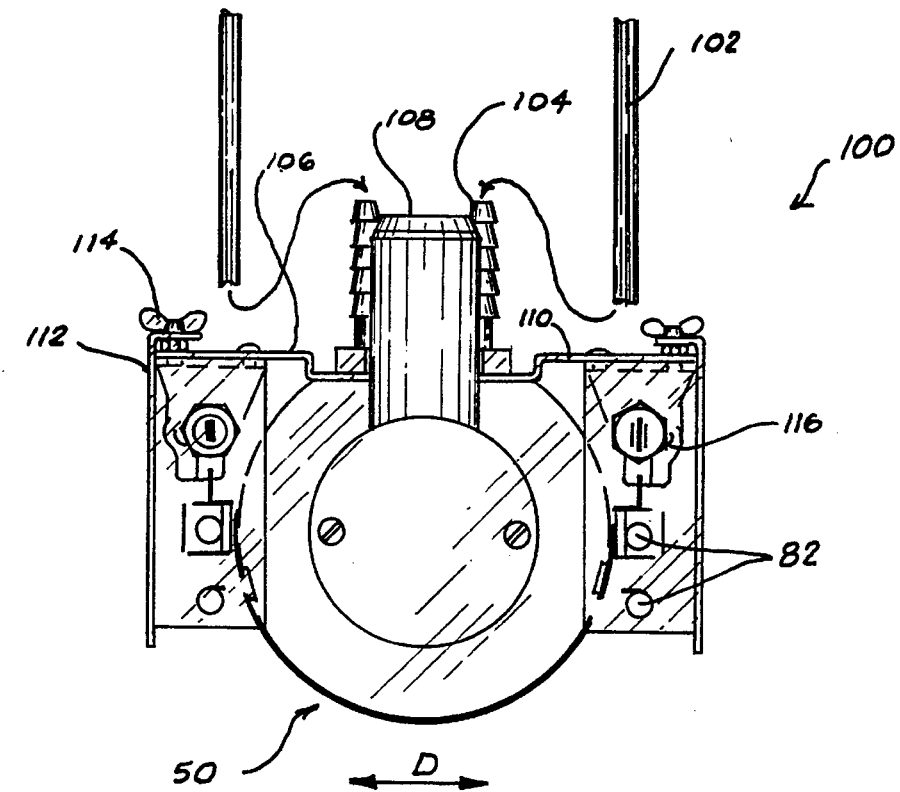
FIG. 3 is an end view of the retrofit assembly for an ultraviolet light sterilization system, according to the present invention.

FIG. 3 shows an end view of a constructed retrofit assembly 100 using ultraviolet light sterilization. Assembly 100 includes, in part, shutter assembly 50, conventional water hoses 102, conventional water hose connectors 104, flange 106, end cap 108, bracket 110, bracket 112, conventional fasteneners 114, reed switch 116 guiding rails 82, and paperboard container conveyor belt travel direction D.

During the operation of shutter assembly 50, pneumatic cylinder 54 is conventionally operated in such a manner that shutter 80 reciprocates along the directions of arrow A such that shutter 80 can be placed directly in front of lamp 4 to block out light emitting from lamp 4 or shutter 80 can be moved such that light from lamp 4 directly contacts food packages and sterilizes the packages.

Figure 4:
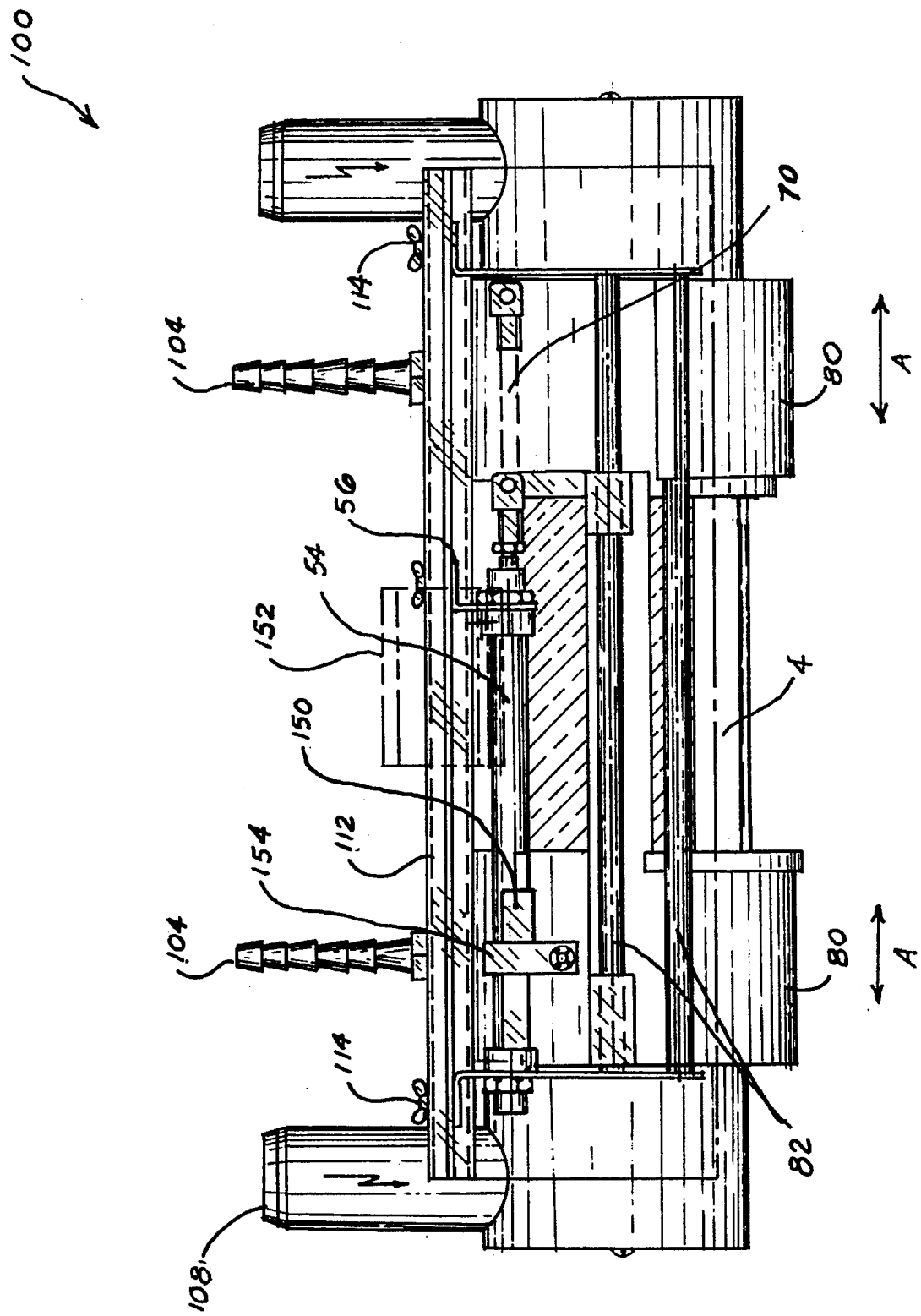
FIG. 4 is a top view of the retrofit assembly for an ultraviolet light sterilization system, according to the present invention.

FIG. 4 illustrates further aspects of retrofit assembly 100. In particular, cover plate 150 and support brackets 152 and 154 can be more clearly seen. Also both sets of shutters 80 are illustrated along with their directions of travel (Arrows A).

During the operation of retrofit assembly 100, paperboard containers (not shown) are transported along a conventional conveyor belt (not shown) and intermittently stopped such that the open end (not shown) of the container is positioned immediately below lamp 4. Preferably, assembly 100 is located perpendicular to the direction of travel D (FIG. 3) of the conveyor belt upon which the containers are located. In this manner, assembly 100 can be more easily retrofitted into existing machines. In this position, lamp 4 is activated such that substantially all of the deleterious microorganisms present on the inner surface of the cartons are eliminated by subjecting this particular surface of the carton to the UV light. This procedure is carried on until the desired number cartons have been sterilized.

However, if during the operation of the retrofit assembly, a malfunction occurs within the assembly 100, reed switch 116 (FIG. 3) is activated. Reed switch 116 should cause the power to lamp 4 to be terminated such that lamp 4 is not activated. Also, reed switch 116 causes shutters 80 to proceed along the directions of arrows A (FIGS. 2 and 4) such that shutters 80 substantially enclose lamp 4 to prevent any harmful substances from contacting lamp 4 or leaves shutter 80 open while assembly 100 is sterilizing containers. It is to be understood that shutters 80 move towards each other and meet substantially half-way along the horizonal length of lamp 4 when totally enclosing lamp 4 and move away from each other when exposing lamp 4. Finally, conventional thermocouple 18 prevents lamp 4 from overheating as discussed earlier.

Also, as assembly 100 is operating, water from a water source (not shown) is transmitted along one of hoses 102 and connectors 104 to lamp 4 and tube 5 through lamp holder 6 and out of the other connector 104 and hose 102. The water is used to cool lamp 4 in an effective and inexpensive manner.

Once given the above disclosure, many other features, modifications or improvements will become apparent to the skilled artisan. Such features, modifications or improvements are, therefore, considered to be a part of this invention, the scope of which is to be determined by the following claims.

What is claimed is:

1. A retrofit assembly for ultraviolet light sterilization of paper packages, wherein said assembly is comprised of:

an individual ultraviolet light;

a light retaining means operatively attached to said light means;

a light covering means operatively connected to said light retaining means, wherein said light covering means is further comprised of:

a bracket means;

a pneumatic cylinder actuation means operatively connected to said bracket means;

a shutter retaining means operatively attached to said actuation means;

a plurality of individually operated shutters operatively attached to said retaining means and positioned adjacent to said light;

a plurality of guide rails operatively connected to said shutter retaining means and said shutter means, wherein said shutters are activated by said activation means and guided along said guide rods in a direction transverse to a direction of movement of a paper package in order to regulate exposure of said package to said light; and a shutter means displacement sensor operatively attached to said shutter means; and a paper package transportation means located a predetermined distance from said light in order that said light can sterilize a predetermined portion of said paper package.

2. The retrofit assembly, as in claim 1, wherein said ultraviolet light is further comprised of:

a temperature controlling means operatively attached to said light for controlling a temperature of said light.

3. The retrofit assembly, as in claim 2, wherein said temperature controlling means is further comprised of:

a thermocouple.

4. The retrofit assembly, as in claim 1, wherein said light retaining means is further comprised of:

a lamp holder means;

a light cooling means operatively connected to said lamp holder means; and a plate rigidly secured to said lamp holder means.

5. The retrofit assembly, as in claim 4, wherein said light cooling means is further comprised of:

a water source;

a water conduit means operatively connected to said water source; and a tube operatively connected to said water conduit means and said light means.

6. The retrofit assembly, as in claim 1, wherein said displacement sensor is further comprised of:

a reed switch.

* * * * *